United States Patent [19]
Wächtler et al.

[11] Patent Number: 4,784,471
[45] Date of Patent: Nov. 15, 1988

[54] 2-FLUOROBENZONITRILE DERIVATIVES AND THEIR USE IN OPTICAL DISPLAY DEVICES

[75] Inventors: Andreas Wächtler, Griesheim; Hans-Adolf Kurmeier, Seeheim/Jugenheim; Reinhard Hittich, Modautal; Bernhard Scheuble, Alsbach, all of Fed. Rep. of Germany

[73] Assignee: Merck Patent Gesellschaft Mit Beschrankter Haftung, Darmstadt, Fed. Rep. of Germany

[21] Appl. No.: 932,544

[22] PCT Filed: Jan. 30, 1986

[86] PCT No.: PCT/EP86/00040
 § 371 Date: Oct. 14, 1986
 § 102(e) Date: Oct. 14, 1986

[87] PCT Pub. No.: WO86/04895
 PCT Pub. Date: Aug. 28, 1986

[30] Foreign Application Priority Data
 Feb. 13, 1985 [DE] Fed. Rep. of Germany ....... 3504866

[51] Int. Cl.[4] .................. G02F 1/13; C07C 121/52
[52] U.S. Cl. .................. 350/350 R; 558/425
[58] Field of Search .................. 558/425; 350/350 R

[56] References Cited
U.S. PATENT DOCUMENTS
4,664,840  5/1987  Osman .................. 558/425

FOREIGN PATENT DOCUMENTS
3339383  5/1985  Fed. Rep. of Germany ...... 558/425

*Primary Examiner*—Mary C. Lee
*Assistant Examiner*—J. Richter
*Attorney, Agent, or Firm*—Millen & White

[57] ABSTRACT

The instant invention relates to compounds of the following formula:

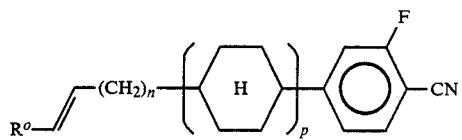

wherein $R^0$ is H or linear alkyl of 1 to 7 C atoms, p is 1 or 2 and n is 0 or 2. The compounds are useful as liquid crystalline compositions in electrooptical display devices.

18 Claims, No Drawings

2-FLUOROBENZONITRILE DERIVATIVES AND THEIR USE IN OPTICAL DISPLAY DEVICES

The invention relates to new fluorobenzene derivatives of the formula I

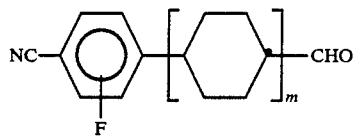

wherein m is 0, 1 or 2 and to reactive derivatives thereof which are particularly suitable for use as intermediate products for the preparation of liquid-crystal compounds, and to the preparation thereof.

The use of liquid-crystal materials for achieving electrooptical effects in display devices, such as, for instance, digital calculators or clocks, is generally known nowadays. One of the parameters of liquid-crystal materials which is important for the operation of electrooptical displays is the dielectric anisotropy ($\Delta\epsilon$) of the material. This is to be understood as meaning, for a given frequency and temperature, the difference between the average dielectric constant ($\epsilon_{II}$) measured parallel to the longitudinal axis of the molecules of the material, for example at a common orientation, and the average dielectric constant ($\epsilon_{I}$) measured perpendicular to the longitudinal axis of the molecules.

The algebraic sign and the amount of the dielectric anisotropy of a given liquid-crystal material constitute one of the most important parameters which define the nature of electrooptical devices in which appropriate materials can be used.

Liquid-crystal materials having a high positive dielectric anisotropy, described in brief as "strongly positive" materials in the following text, can, for example, be used in known twisted-nematic devices. For example, mixtures of 4-alkylcyanobiphenyls, p-4-alkylcyclohexylbenzonitriles and 4-cyano-4'-(4-alkylcyclohexyl)-biphenyls have been introduced for applications of this type to an extent which is of economic importance.

Liquid-crystal materials having a small positive dielectric anisotropy, described in brief as "weakly positive" materials in the following text, can be mixed either with strongly positive materials or with strongly negative materials in order to modify the dielectric anisotropy.

The compounds of the formula I can be used like similar, not laterally fluorinated compounds, for example, like the compounds listed in German Offenlegungsschrift No. 2,944,905, as intermediates products for the synthesis of liquid-crystal materials of high or low positive dielectric anisotropy.

The invention was based on the object of indicating fluorobenzene derivatives, and the preparation thereof, which are suitable for the particularly simple synthesis of liquid-crystal compounds having a weakly positive or strongly positive dielectric anisotropy.

It has now been found that the compounds of the formula I are excellently suitable for the one-stage synthesis of a large number of target products.

In addition, the provision of the compounds of the formula I considerably widens, in a very general manner, the range of intermediate products suitable from various aspects for the preparation of liquid crystals.

The invention relates, therefore, to the fluorobenzene derivatives of the formula I

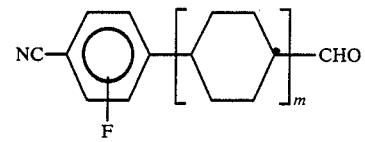

wherein m is 0, 1 or 2, to reactive derivatives thereof and to a process for their preparation, characterised in that, in order to prepare cyclohexanecarbaldehydes of the formula I (m=1 or 2), a compound of the formula II

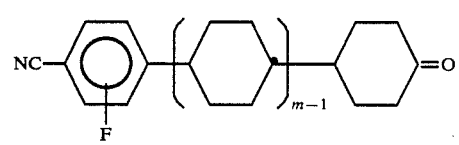

is reacted, in the presence of a base, with a triphenylalkoxymethylphosphonium halide, and the resulting alkoxymethylene compound is treated with an acid, or, in order to prepare benzaldehydes of the formula I (m=0), a compound of the formula III

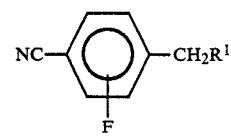

wherein $R^1$ is halogen or OH, or reactive derivatives thereof, is oxidised, or a compound of the formula IV

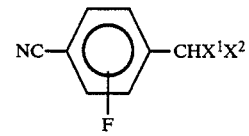

wherein
$X^1$ and $X^2$ are each halogen or $X^1$ and $X^2$ together are =NOH
is hydrolysed, or a compound of the formula V

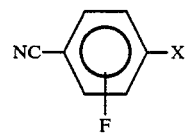

wherein
X is halogen, a monovalent metal or a corresponding equivalent is formylated,
or a compound of the formula VI

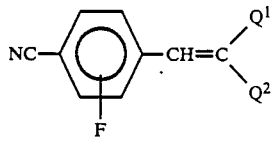

wherein

Q¹ and Q² independently of one another are H, alkyl or unsubstituted or substituted aryl or aralkyl is treated with ozone, and the resulting ozonide is subjected to reductive cleavage.

The invention also relates to the use of fluorobenzene derivatives of the formula I, according to claim 1, as intermediate products in the preparation of liquid-crystal materials.

The fluorobenzene derivatives of the formula I and reactive derivatives thereof can be used, in accordance with the invention, as intermediate products for the preparation of liquid-crystal materials, it being possible to react them, for example, with propane-1,3-diols which are substituted in the 2-position to give corresponding 1,3-dioxane compounds or with alkyltriphenylphosphonium halides analogously to European Published Application No. 0,122,389 to give corresponding alkylene compounds.

Suitable reactive derivatives of compounds of the formula I are primarily acetals of the formula Ia:

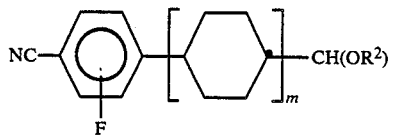

wherein R² is alkyl having 1 to 4C atoms, two radicals R² together also being alkylene having 2 to 3C atoms, and also carboxylic acids (or acid halides thereof) of the formula Ib:

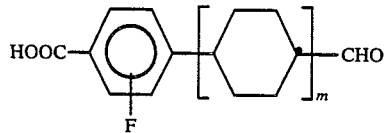

Carboxylic acids of the formula Ib or reactive derivatives thereof can, after esterification with suitable phenols or cyclohexanols, be reacted as described above, for example to give 1,3-dioxane derivatives or, in accordance with European Published Application No. 0,122,389, to give alkenyl compounds.

The preparation of the fluorobenzene derivatives according to the invention is illustrated by examples in diagram 1 below.

The intermediate product ethyl 4-cyano-3-fluorobenzoate from Diagram 1 can also be obtained by oxidizing 2-fluoro-4-methylbenzonitrile and esterifying the resulting benzoic acid, or in accordance with the following sequence of reactions:

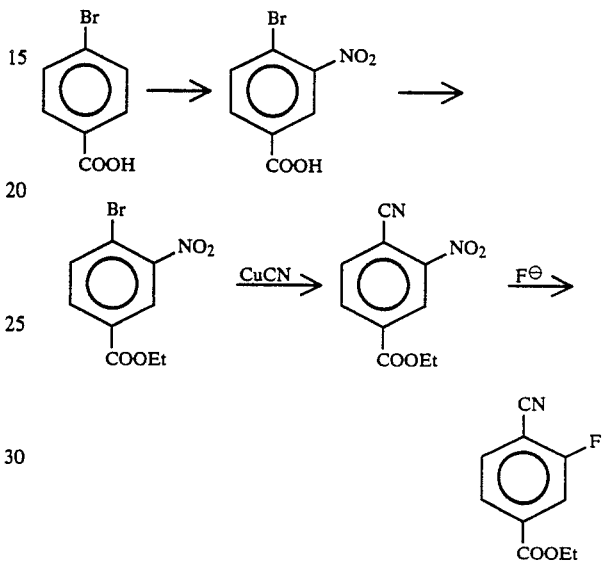

Instead of the benzyl halides listed in diagram 1, the oxidation of which gives the fluorobenzene derivatives according to the invention, it is also possible to employ the corresponding dihalides (formula IV, X¹=halogen, X²=halogen), hydrolysis of which by known methods gives the compounds of the formula I.

The compounds of the formula I can be prepared in accordance with diagram 1 by methods which are in themselves known, such as are described in the literature (for example in the standard works, such as Houben-Weyl, Methoden der organischen Chemie [Methods of Organic Chemistry], Georg-Thieme-Verlag, Stuttgart), under reaction conditions which are known and suitable for the reactions mentioned. In this respect it is also possible to make use of variants which are in themselves known but are not mentioned here in detail. All the starting materials are known from the literature.

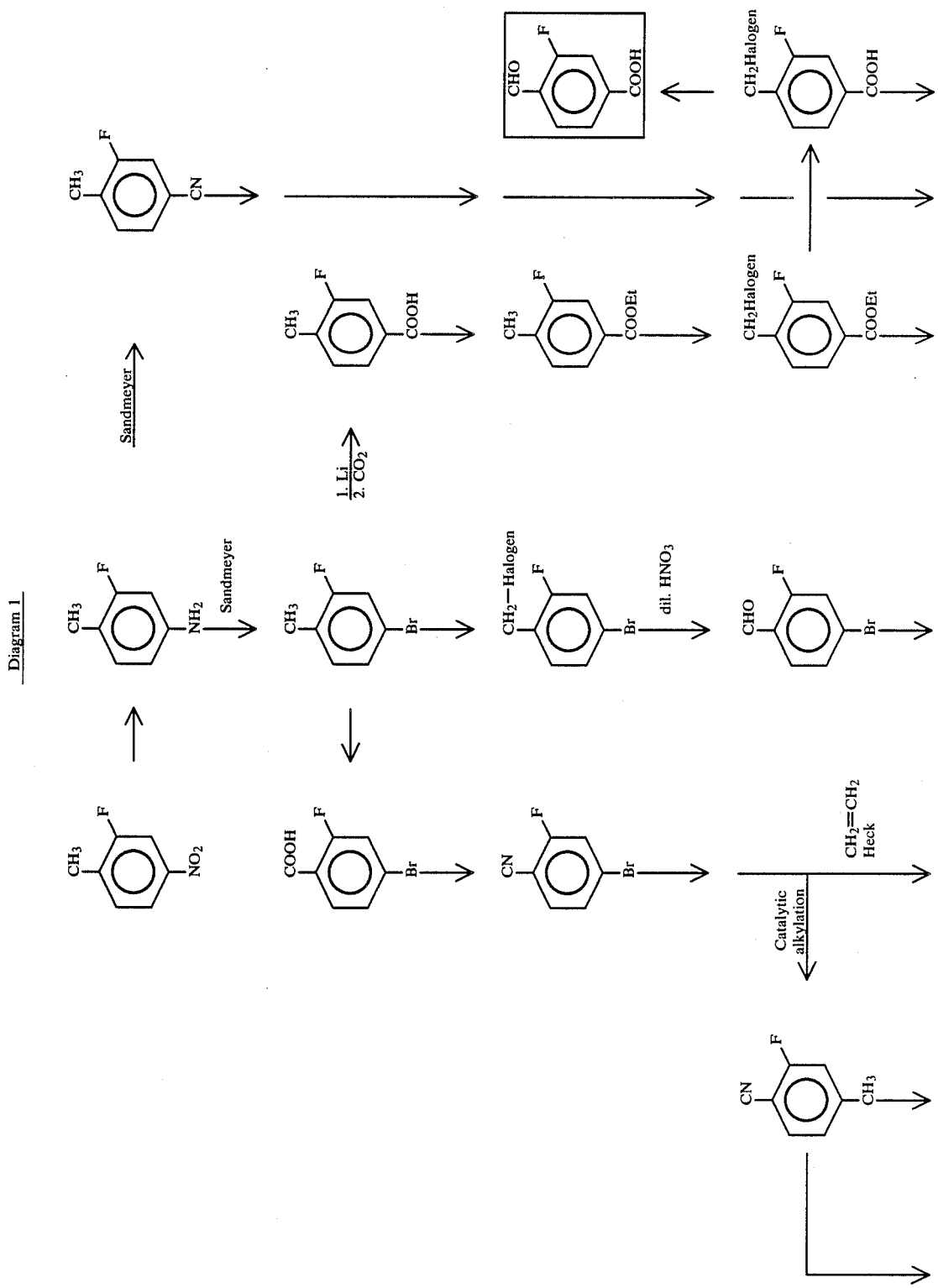

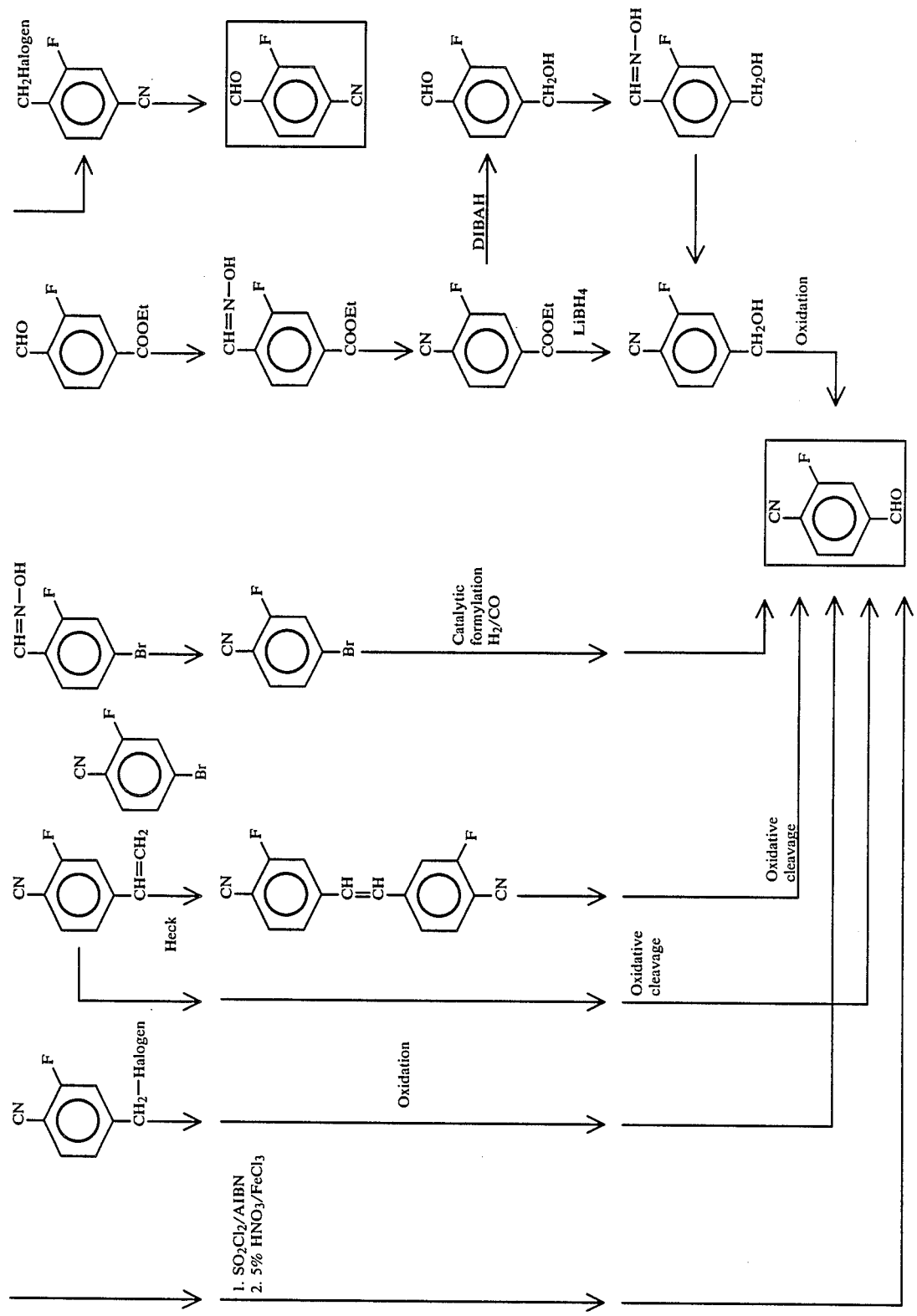

Preferred starting materials are the commercially available chemicals 2-fluoro-4-nitrotoluene, 2-fluoro-4-aminotoluene and p-bromobenzoic acid as well as 2-fluoro-4-methylbenzonitrile, which is known from the literature (European Published Application No. 0,061,907), which can be reacted by methods known from the literature in accordance with diagram 1 to give precursors of the formulae III, IV, V and VI.

Precursors of the formula III wherein $R^1$ is preferably halogen, in particular chlorine, bromine or iodine, or OH can be converted by oxidation into the fluorobenzene derivatives, according to the invention, of the formula I. Examples of suitable oxidising agents for the benzyl alcohols of the formula III are chromic acid, the $CrO_3$-pyridine complex, dichromate/sulfuric acid, pyridine dichromate, nitric acid, manganese dioxide or selenium dioxide. Oxidation with tert.-butyl chromate in petroleum ether, benzene or carbon tetrachloride or with manganese dioxide in acetone, petroleum ether, carbon tetrachloride or dilute sulfuric acid is particularly preferred.

The benzyl alcohols can also be oxidised indirectly, by known methods, via appropriate reactive derivatives (for example tosyl esters). The benzyl alcohols can also be converted into the fluorobenzene derivatives according to the invention by treatment with dimethyl sulfoxide, dicyclohexylcarbodiimide or phosphoric acid.

The benzyl halides, in particular the benzyl bromides, of the formula III can be oxidised to the fluorobenzene derivatives according to the invention, for example in accordance with methods known from the literature by treatment with dimethyl sulfoxide, hexamethylenetetramine, 2-nitropropane/NaOET in EtOH, trimethylamine oxide or potassium dichromate in HMPT in the presence of a crown ether.

Compounds of the formula IV can be converted into the fluorobenzene derivatives according to the invention in accordance with methods known from the literature (oximes, for example, by treatment with aqueous acids, $NaHSO_3$ or lead tetraacetate).

The compounds of the formula I can also be obtained by formylating compounds of the formula V wherein X is halogen, preferably bromine.

The compounds of the formula V are reacted with a $CO/H_2$ mixture (preferably 1:2 to 2:1, in particular 1:1), preferably under catalytic conditions in the presence of a base at temperatures between room temperature and 220°, preferably 80° to 150°, under a pressure of 40 to 160 atmospheres, preferably 60 to 100 atmospheres. The bases employed are preferably tertiary amines and the catalyst is preferably dihalogeno-bis-(triphenylphosphine)-palladium-(III). Compounds of the formula V wherein X is a monovalent metal, preferably lithium, can be converted into the fluorobenzene derivatives according to the invention, for example in accordance with known methods by reaction with N-formylpiperidine. Lithium compounds of the formula V can also be reacted with dihydro-1,3-oxazines in accordance with known methods. The resulting addition products can be hydrolysed to give fluorobenzene derivatives of the formula I.

Compounds of the formula V wherein X is Mghalogen can be converted into fluorobenzene derivatives of the formula I in accordance with known methods by reaction with N-alkyl derivatives of 2-oxazolines in the presence of HMPT.

A further variant for the preparation of the fluorobenzene derivatives according to the invention is the reaction of compounds of the formula VI with ozone and subsequent reductive cleavage of the resulting ozonides. $Q^1$ is preferably H or lower alkyl having 1 to 4C atoms and $Q^2$ is preferably H. Particularly preferably $Q^1=Q^2=H$. Compounds of the formula VI which are also particularly preferred are those wherein $Q^1=H$ and $Q^2$ is 4-cyano-3-fluorophenyl. In the subsequent ozonolysis, these compounds of the formula VI produce a reaction mixture which is particularly easy to work up.

The ozonolysis of the compounds of the formula VI is carried out in a customary manner in inert solvents, such as carbon tetrachloride, ethyl acetate or alcohols (in particular methanol) or acetic acid, at low temperatures. The reductive cleavage of the ozonides is preferably effected by means of reducing agents, such as zinc/acetic acid, trimethyl phosphite, sodium dithionite and, particularly preferentially, dimethyl sulfide, or by catalytic hydrogenation, for example over palladium-on-calcium carbonate.

The fluorobenzene derivatives according to the invention can also be obtained from corresponding aryl oximes [obtainable from the corresponding diazonium salts by reaction with oximes] by hydrolysis using the method of W. F. Beech, J. Chem. Soc. 1297 (1954) in the presence of a copper sulfate/sodium sulfite catalyst.

The intermediate products indicated in Diagram 1 are in part new and also form a subject of the invention. Special mention should be made here of the intermediate products of the formula

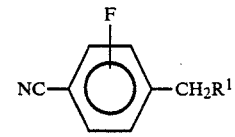

wherein $R^1$ is halogen or OH or reactive derivatives thereof. The 2-fluorobenzonitrile derivatives of the above formula are particularly preferred.

The present invention also relates to new compounds of the formula A

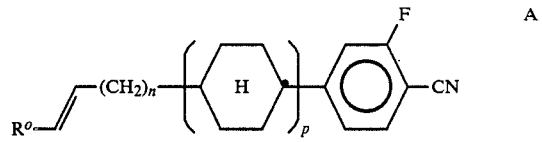

wherein $R^o$ is H or linear alkyl having 1 to 7C atoms, p is 1 or 2 and n is 0 or 2. The compounds of the formula A are accessible analogously to European Published Application No. 0,122,389 from the compounds of the formula I (m=1 or 2), and are distinguished by a particularly high positive dielectric anisotropy, low viscosity, improved mesophase behaviour and advantageous elastic properties. The compounds, according to the invention, of the formula A are very suitable for use as liquid-crystal phases in electrooptical display elements.

The examples which follow are intended to illustrate the invention, without limiting it. In the examples, m.p. is the melting point of a substance and b.p. is its boiling point. In the preceding and following text percentages are percentages by weight; all temperatures are indicated in degrees celsius. "Customary working up" means as follows: water is added, the mixture is extracted with methylene chloride, the phases are separated, the organic phase is dried and evaporated and the product is purified by distillation, crystallisation and/or chromatography.

EXAMPLE 1

1.8 g of solid potassium t.-butylate are added at −15° to a suspension of 5.3 g of triphenylmethoxymethylphosphonium chloride in 100 ml of diisopropyl ether, and the mixture is stirred for a further 30 minutes. A solution of 2.3 g of 4-(4-cyano-3-fluorophenyl)-cyclohexanone [obtainable by reacting 4-bromo-2-fluorobenzonitrile and cyclohexane-1,4-dione monoethylene ketal with butyllithium in ether at −100° by the method of W. E. Porham and L. D. Jones, J. Org. Chem. 41, 1187, 2704 (1976), subsequently eliminating water from the resulting cyclohexanol, hydrogenating the double bond and splitting off the ethylene ketal protective group] in 30 ml of THF is then added dropwise to the suspension, and the reaction mixture is stirred for a further 3 hours at room temperature, then poured into 300 ml of petroleum ether and filtered. Working up the filtrate in the customary manner gives 4-[4-(methoxymethylene)cyclohexyl]-2-fluorobenzonitrile as a colourless oil. A mixture of 1.0 g of this oil, 20 ml of THF and 5 ml of 2N hydrochloric acid is boiled for 30 minutes and then worked up in the customary manner. Trans-4-(4-cyano-3-fluorophenyl)-cyclohexanecarbaldehyde is obtained after crystallisation.

Trans-4-(4-cyano-fluorophenyl)-cyclohexanecarbaldehyde is obtained analogously from 4-bromo-3-fluorobenzonitrile.

EXAMPLE 2

A mixture of 5.0 g of 4-bromo-2-fluorobenzonitrile [obtainable from 4-amino-2-fluorotoluene by conversion into 4-bromo-2-fluorotoluene (b.p./12: 55°-57°), subsequent bromination with N-bromosuccinimide to give 4-bromo-2-fluorobenzyl bromide (b.p./14: 125°-130°), subsequent oxidation with dilute nitric acid to give 4-bromo-2-fluorobenzaldehyde, subsequent reaction to give 4-bromo-2-fluorobenzaldoxime and subsequent conversion into the target product (m.p. 70°)], 10 ml of toluene, 10 ml of triethylamine and 0.3 g of $(Pph_3)_2PdBr_2$ was stirred for 24 hours at 145° in an autoclave at a pressure of 80 atmospheres of synthesis gas (CO: $H_2$ =1:1) by the method of R. F. Heck and A. Schonberg, J. Am. Chem. Soc. 96, 7761 (1974). Cooling and working up in the customary manner gives 3-fluoro-4-cyanobenzaldehyde) m.p. 83°.

EXAMPLE 3

46 g of 2-nitropropane and 107 g of 2-fluoro-4-cyanobenzylbromide [obtainable by free-radical bromination of 2-fluoro-4-cyanotoluene, which can be obtained from 2-fluoro-4-aminotoluene by a Sandmeyer reaction; alternatively, 2-fluoro-4-cyanobenzyl bromide can be obtained from 2-fluoro-4-bromotoluene by reaction with butyllithium and N-formylpiperidine, giving 3-fluoro-4-methylbenzaldehyde, which is subsequently converted into the oxime and water is eliminated from it] are added successively to a solution of 11.5 g of sodium in 500 ml of ethanol. After being stirred for 4 hours, the reaction mixture is filtered, concentrated and worked up in the customary manner. This gives 2-fluoro-p-cyanobenzaldehyde.

EXAMPLE 4

An equimolar amount of ozone is introduced, at −70° and with stirring, in the course of one hour, into a mixture of 13.3 g of 4,4′-dicyano-3,3′-difluorostilbene [obtainable from 4-bromo-2-fluorobenzonitrile by a double Heck reaction with ethylene or 4-cyano-3-fluorostyrene by the method of R. W. Heck, Palladium-Catalysed Vinylation of Organic Halides, Organic Reactions 27, 345 (1982)] and 150 ml of anhydrous methanol. The resulting ozonide is then subjected to cleavage by adding 31.1 g of dimethyl sulfide at −70°. The reaction mixture is allowed to warm up to room temperature with stirring in the course of 2 hours and is stirred for a further hour. After the solvent has been removed, the residue is worked up in the customary manner. This gives 4-cyano-3-fluorobenzaldehyde.

EXAMPLE 5

40 g of ethyl 4-cyano-3-fluorobenzoate in 40 ml of THF are added dropwise to a solution of 8 g of $LiBH_4$ in 120 ml of THF. In the course of this, the reaction mixture comes to the boil. After one hour it is acidified with 2NHCl and worked up in a customary manner. 3-Fluoro-4-cyanobenzyl alcohol, m.p. 70°-72° C., is obtained.

EXAMPLE 6

A solution of 22 g of 3-fluoro-4-cyanobenzyl alcohol in 50 ml of methylene chloride is added, with stirring, to 48 g of PCC in 150 ml of methylene chloride. After one hour 300 ml of methyl tert.-butyl ether are added to the reaction mixture and the latter is filtered, with the addition of Celite. Removing the solvent and recrystallising the residue from aqueous ethanol gives 3-fluoro-4-cyanobenzaldehyde, m.p. 83°-85°, IR ($cm^{-1}$): 3089, 2880, 2239, 1699, 1571, 1499, 1486, 1428, 1392, 1299, 1251, 1140, 1111, 971, 900, 839, 753; $^1$H-NMR (200 MHz): (ppm): 7.7-8.0 (m, 3H, aromatic), 10.1 (s, 1H, CHO).

The following examples relate to the use of the fluorobenzene derivatives of the formula I for the preparation of liquid-crystal materials.

EXAMPLE A 7.4 ml of 1.7M n-butyllithium in hexane are added, with stirring and under an atmosphere of nitrogen, to a suspension of 5.4 g of n-butyltriphenylphosphonium bromide in 100 ml of ether. After 30 minutes the orange solution is cooled to −40° and 2.1 g of 4-(3-fluoro-4-cyanophenyl)-cyclohexanecarbaldehyde in 20 ml of ether are added. After stirring for 2 hours at −40°, 60 ml of ethanol are added dropwise. The reaction mixture is then allowed to warm up to room temperature, is stirred for one hour and worked up in the customary manner. 2-fluoro-4-[trans-4-(trans-1-pentenyl)-cyclohexyl]-benzonitrile is obtained after isomerisation in the customary manner analogously to European Published Application No. 0,122,389.

The following are prepared analogously:
2-fluoro-4-[trans-4-(trans-1-propenyl)-cyclohexyl]-benzonitrile
2-fluoro-4-[trans-4-(trans-1-butenyl)-cyclohexyl]-benzonitrile
2-fluoro-4-[trans-4-(trans-1-hexenyl)-cyclohexyl]-benzonitrile
2-fluoro-4-[trans-4-(trans-1-heptenyl)-cyclohexyl]-benzonitrile The following are also prepared analogously to European Published Application No. 0,122,389:

2-fluoro-4-[trans-4-(trans-3-butenyl)-cyclohexyl]-benzonitrile 2-fluoro-4-[trans-4-(trans-3-pentenyl)-cyclohexyl]-benzonitrile 2-fluoro-4-[trans-4-(trans-3-hexenyl)-cyclohexyl]-benzonitrile 2-fluoro-4-[trans-4-(trans-3-heptenyl)-cyclohexyl]-benzonitrile.

EXAMPLE B

A mixture of 2.3 g of trans-4-(4-cyano-3-fluorophenyl)-cyclohexanecarbaldehyde, 1.2 g of 2-propyl-propane-1,3-diol, 0.01 g of p-toluenesulfonic acid and 15 ml of toluene is boiled for 3 hours under a water separator and is cooled. Working up in the customary manner gives 2-[trans-4-(4-cyano-3-fluorophenyl)-cyclohexyl]-5-propyl-1,3-dioxane.

The following are prepared analogously:

2-[trans-4-(4-cyano-3-fluorophenyl)-cyclohexyl]-5-ethyl-1,3-dioxane

2-[trans-4-(4-cyano-3-fluorophenyl)-cyclohexyl]-5-butyl-1,3-dioxane

2-[trans-4-(4-cyano-3-fluorophenyl)-cyclohexyl]-5-pentyl-1,3-dioxane

2-[trans-4-(4-cyano-3-fluorophenyl)-cyclohexyl]-5-hexyl-1,3-dioxane

2-[trans-4-(4-cyano-3-fluorophenyl)-cyclohexyl]-5-hexyl-1,3-dioxane, 2-(4-cyano-3-fluorophenyl)-5-ethyl-1,3-dioxane 2-(4-cyano-3-fluorophenyl)-5-propyl-1,3-dioxane, m.p. 49°, $\Delta\epsilon=31$ 2-(4-cyano-3-fluorophenyl)-5-butyl-1,3-dioxane 2-(4-cyano-3-fluorophenyl)-5-pentyl-1,3-dioxane 2-(4-cyano-3-fluorophenyl)-5-hexyl-1,3-dioxane 2-(4-cyano-3-fluorophenyl)-5-heptyl-1,3-dioxane.

EXAMPLE C

A mixture of 2-fluoro-4-(p-pentylphenoxycarbonyl)-benzaldehyde (obtainable from 3-fluoro-4-formylbenzoic acid by esterification with p-pentylphenol) and 2-propylpropane-1,3-diol is treated analogously to Example B. This gives p-pentylphenyl 3-fluoro-4-(5-propyl-1,3-dioxan-2-yl)-benzoate.

The following are prepared analogously:

p-Propylphenyl 3-fluoro-4-(5-propyl-1,3-dioxan-2-yl)-benzoate p-Ethylphenyl 3-fluoro-4-(5-propyl-1,3-dioxan-2-yl)-benzoate p-Ethoxyphenyl 3-fluoro-4-(5-propyl-1,3-dioxan-2-yl)-benzoate p-Butoxyphenyl 3-fluoro-4-(5-propyl-1,3-dioxan-2-yl)-benzoate p-Cyanophenyl 3-fluoro-4-(5-propyl-1,3-dioxan-2-yl)-benzoate Trans-4-ethylcyclohexyl 3-fluoro-4-(5-propyl-1,3-dioxan-2-yl)-benzoate Trans-4-propylcyclohexyl 3-fluoro-4-(5-propyl-1,3-dioxan-2-yl)-benzoate Trans-4-butylcyclohexyl 3-fluoro-4-(5-propyl-1,3-dioxan-2-yl)-benzoate Trans-4-pentylcyclohexyl 3-fluoro-4-(5-propyl-1,3-dioxan-2-yl)-benzoate Trans-4-heptylcyclohexyl 3-fluoro-4-(5-propyl-1,3-dioxan-2-yl)-benzoate.

What is claimed is:

1. A compound of the formula:

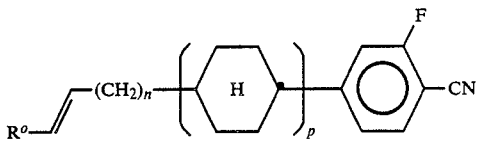

wherein R° is H or linear alkyl of 1 to 7C atoms, p is 1 or 2 and n is 0 or 2.

2. A fluoro-4-[trans-4-(trans-1-pentenyl)-cyclohexyl]-benzonitrile, a compound of claim 1.

3. 2-fluoro-4-[trans-4-(trans-1-propenyl)-cyclohexyl]-benzonitrile, a compound of claim 1.

4. 2-fluoro-4-[trans-4-(trans-1-butenyl)-cyclohexyl]-benzonitrile, a compound of claim 1.

5. 2-fluoro-4-[trans-4-(trans-1-hexenyl)-cyclohexyl]-benzonitrile, a compound of claim 1.

6. 2-fluoro-4-[trans-4-(trans-1-heptenyl)-cyclohexyl]-benzonitrile, a compound of claim 1.

7. 2-fluoro-4-[trans-4-(trans-3-butenyl)-cyclohexyl]-benzonitrile, a compound of claim 1.

8. 2-fluoro-4-[trans-4-(trans-3-pentenyl)-cyclohexyl]-benzonitrile, a compound of claim 1.

9. 2-fluoro-4-[trans-4-(trans-3-hexenyl)-cyclohexyl]-benzonitrile, a compound of claim 1.

10. 2-fluoro-4-[trans-4-(trans-3-heptenyl)-cyclohexyl]-benzonitrile, a compound of claim 1.

11. In a liquid-crystal phase comprising at least two liquid crystalline components, the improvement wherein at least one component is a compound of claim 1.

12. In an electrooptical display element comprising a liquid crystal phase, the improvement wherein the phase is one of claim 11.

13. A compound of claim 1 wherein p=1.

14. A compound of claim 1 wherein p=2.

15. A compound of claim 1 wherein n=0.

16. A compound of claim 1 wherein n=2.

17. A compound of claim 15 wherein R° is linear alkyl of 1–5C atoms.

18. A compound of claim 16 wherein R° is H or linear alkyl of 1–3C atoms.

* * * * *